United States Patent [19] [11] 4,070,368
Carson [45] Jan. 24, 1978

[54] PROCESS FOR PREPARING ALKYL, AROYL SUBSTITUTE PYRROLE-2-ACETATES

[75] Inventor: John Robert Carson, Norristown, Pa.

[73] Assignee: McNeil Laboratories, Incorporated, Fort Washington, Pa.

[21] Appl. No.: 479,733

[22] Filed: June 17, 1974

Related U.S. Application Data

[60] Division of Ser. No. 338,461, Feb. 16, 1973, Pat. No. 3,865,840, which is a division of Ser. No. 5,958, Jan. 26, 1970, Pat. No. 3,752,826, which is a continuation-in-part of Ser. No. 741,348, July 1, 1968, abandoned, which is a continuation-in-part of Ser. No. 656,074, July 26, 1967, abandoned.

[51] Int. Cl.² ........................................... C07D 207/34
[52] U.S. Cl. ................................................ 260/326.47
[58] Field of Search ....................... 260/326.46, 326.47

[56] References Cited

FOREIGN PATENT DOCUMENTS

| 9,088/62 | 7/1962 | Japan | 260/326.46 |
|---|---|---|---|
| 10,509/67 | 6/1967 | Japan | 260/326.46 |
| 24,897/67 | 11/1967 | Japan | 260/326.46 |
| 43-17963 | 7/1968 | Japan | 260/326.46 |

OTHER PUBLICATIONS

Paquette et al, J. Organic Chem., 27, pp. 2272–2274(1962).
Chase et al, J. Chem. Soc., pp. 553–571 (at page 565), 1952.
Patal, S. (Ed), "The Chemistry of Carboxylic Acids and Esters", p. 199, Interscience, N. Y. 1969.
Rips et al "J. Org. Chem.", vol. 24, pp. 551–554, (1959).

*Primary Examiner*—Paul M. Coughlan, Jr.
*Assistant Examiner*—D. B. Springer
*Attorney, Agent, or Firm*—Salvatore R. Conte; Alice O. Robertson

[57] ABSTRACT

The compounds are of the class of 5-aroyl-pyrrole alkanoic acids and corresponding acid derivatives thereof useful as anti-inflammatory agents and as synthetic intermediates.

2 Claims, No Drawings

PROCESS FOR PREPARING ALKYL, AROYL SUBSTITUTE PYRROLE-2-ACETATES

This is a divisional application of my copending application Ser. No. 338,461, filed Feb. 16, 1973, issued as U.S. Pat. No. 3,865,840 on Feb. 11, 1975, which in turn is a divisional application of application Ser. No. 5,958, filed Jan. 26, 1970, issued as U.S. Pat. No. b 3,752,826 on Aug. 14, 1973, which in turn is a continuation-in-part application of application Ser. No. 741,348, filed July 1, 1968, now abandoned, which in turn is a continuation-in part application of application Ser. No. 656,074, filed July 26, 1967, now abandoned.

This invention relates to novel 5-aroyl-pyrroles, and, more particularly, to 5-aroyl-pyrrole alkanoic acids and the corresponding salts, esters, nitriles, amides and substituted amides thereof. Said 5-aroyl-pyrroles may be represented by the following formulas:

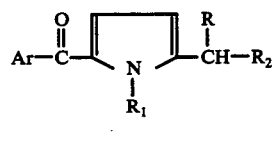

(I-a),

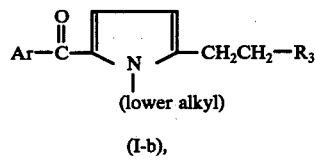

(I-b),

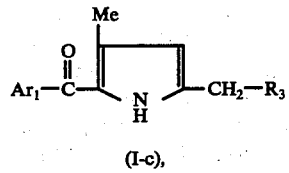

(I-c),

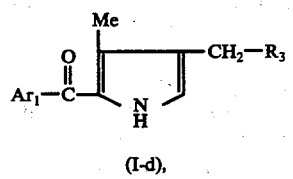

(I-d), and

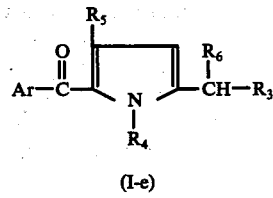

(I-e)

wherein:
Ar represents a member selected from the group consisting of phenyl, thienyl, 3-methylthienyl, monosubstituted phenyl and polysubstituted phenyl, each substituent of said substitute phenyls being a member selected from the group consisting of halo, lower alkyl, trifluoromethyl, lower alkoxy, nitro, amino, cyano and methylthio;

$Ar_1$ represents a member selected from the group consisting of phenyl, monosubstituted phenyl and polysubtituted phenyl, each substituent of said substituted phenyls being a member selected from the group consisting of halo, lower alkyl and lower alkoxy;

R represents a member selected from the group consisting of hydrogen and lower alkyl;

$R_1$ represents a member selected from the group consisting of hydrogen, lower alkyl and benzyl;

$R_2$ represents a member selected from the group consisting of CN, COOH, COO-(lower alkyl), $CONH_2$, CONH-(lower alkyl), CON-(lower alkyl)$_2$, CONH—OH and CONH-$(CH_2)_n$-N(lower alkyl)$_2$ in which $n$ is an integer of from 2 to 4 carbon atoms;

$R_3$ represents a member selected from the group consisting of COOH, COO-(lower alkyl), $CONH_2$, CONH-(lower alkyl) and CON-(lower alkyl)$_2$;

$R_4$ represents lower alkyl;

$R_5$ represents lower alkyl; and $R_6$ represents a member selected from the group consisting of hydrogen and lower alkyl;

provided that:
i. when said Ar is a member selected from the group consisting of nitro-substituted phenyl and amino-substituted phenyl, then, with regard to Formula (I-a), said R is hydrogen, said $R_1$ is lower alkyl and said $R_2$ is a member selected from the group consisting of CN, COOH and COO-(lower alkyl); and with regard to Formula (I-e), said $R_6$ is hydrogen;

ii. when said Ar is cyanophenyl, then said $R_1$ is lower alkyl and said $R_2$ is a member selected from the group consisting of COOH and COO-(lower alkyl); and iii. when said $R_1$ is hydrogen, then said R is hydrogen.

The non-toxic, therapeutically acceptable salts of such acids, such as are obtained from appropriate organic or inorgaic bases, are also embraced within the scope of this invention.

As used herein, "lower alkyl" and "lower alkoxy" may be straight or branch chained saturated hydrocarbons having from 1 to 6 carbon atoms, such as, for example, methyl, ethyl, propyl, isopropyl, butyl, pentyl, hexyl and the like alkyls, and, respectively, the corresponding alkoxys such as methoxy, ethoxy, propoxy, isopropoxy, etc.

The subject compounds may be obtained by means of several synthetic processes. For example, the compounds of formula (I-a), in which $R_2$ is CN or COO-(lower alkyl), are generally prepared by a Friedel-Crafts reaction between an appropriate aroyl halide, preferably the chloride (II), and a pyrrole-2-acetic acid derivative of formula (III), wherein R' is cyano or lower alkoxy-carbonyl, in the presence of a Lewis acid, preferably a metallic halide such as aluminum chloride. Suitable solvents are those typically employed in a Friedel-Crafts reaction, such as, for example, methylene chloride, 1,2-dichloroethane, carbon disulfide, nitrobenzene and the like. The acid derivative (IV) thus obtained can then be converted to the corresponding free carboxylic acid by conventional hydrolysis, for example, by heating a solution of (IV) in aqueous methanol with an alkali metal hydroxide to form the alkali metal salt of the acid and then acidifying the mixture. The foregoing reactions may be illustrated by the following schematic diagram.

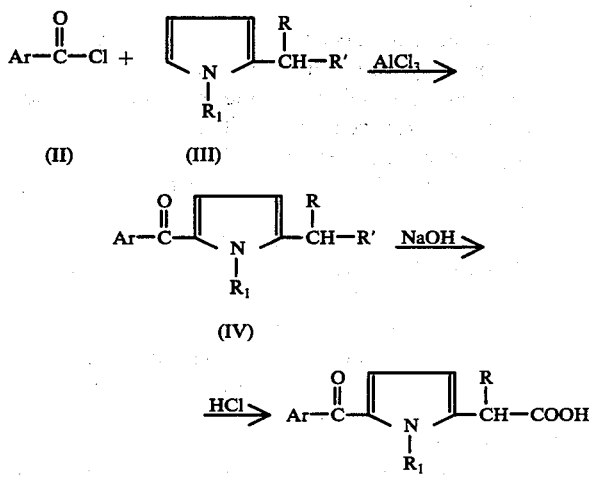

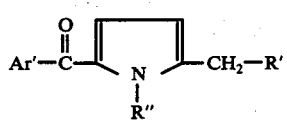

The aroyl chlorides (II) are generally known and may be obtained by transformation of the corresponding acid to the acid chloride form according to conventional procedures, such as, for example, the procedure hereinafter demonstrated in Example LXXXI.

Alternatively, to prepare the nitriles, esters and acids of formula (I-a), wherein R is lower alkyl, a 5-aroylpyrrole-2-acetic acid derivative of the formula:

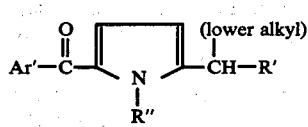

wherein R' is as previously described, R" is lower alkyl or benzyl, and Ar'O is thienyl, 5-methylthienyl, phenyl or phenyl substituted with halo, lower alkyl, trifluoromethyl, methylthio, lower alkoxy or cyano, which acid derivative (V) may be obtained in accordance with the aforementioned Friedel-Crafts procedure, is alkylated according to conventional alkylation techniques, e.g., with a lower alkyl halide as the alkylating agent in the presence of a strong base such as sodium amide or sodium hydride, to yield the corresponding nitriles and esters:

from which the corresponding acids are obtained by conventional hydrolysis.

The acetonitriles of formula (VI), in which R" is lower alkyl, are also obtained by conventional N-alkylation of an N-unsubstituted 5-aroyl-pyrrole-2-acetonitrile of the formula:

(VII)

followed by conventional C-alkylation of the thus-obtained N-alkyl-5-aroyl-pyrrole-2-acetonitrile using an appropriate lower alkyl halide as the alkylating agent in each step. After the N-alkylation step or the C-alkylation step, corresponding acids may be obtained by conventional hydrolysis.

The nitriles, esters and acids of formula (I-a), wherein Ar is amino-substituted phenyl, are preferably prepared from the corresponding 5-nitrobenzoyl-1-(lower alkyl)-pyrrole-2-acetic acid esters of nitriles according to the following reaction scheme in which the corresponding para-derivatives are exemplified (R' being as previously described):

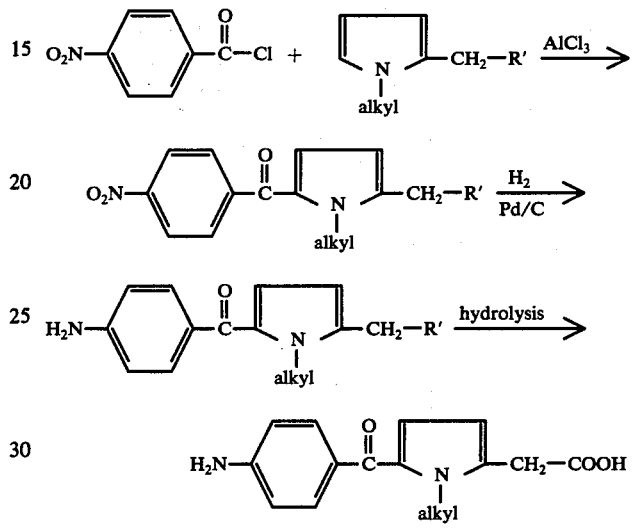

In the foregoing reaction sequence, the nitro function of the 5-nitrobenzoyl-1-(lower alkyl)-pyrrole-2-acetic acid ester or nitrile (obtained by the Friedel-Crafts type of reaction previously described) is catalytically hydrogenated, for example, with hydrogen and palladium-on-carbon catalyst, to yield the corresponding 5-aminobenzoyl-1-(lower alkyl)-pyrrole-2-acetic acid ester or nitrile which is then hydrolzed to the corresponding free acid form.

Esterification of the acids of formula (I-a) with a slight excess of an appropriate lower alkanol yields the corresponding esters, i.e., wherein $R_2$ equals COO-(lower alkyl). Preferably, the methyl esters of formula (I-a) are obtained by the Friedel-Crafts reaction previously described between an appropriate aroyl halide (II) and an appropriate methyl pyrrole-2-acetate (III).

The primary amides of formula (I-a) are readily obtained by partial hydrolysis of the corresponding nitriles of formula (I-a). The nitrile-to-amide transformation is accomplished according to conventional procedures, for example, by treatment of the nitrile with aqueous sodium hydroxide under reflux for a relatively short time, that is, a period sufficient for partial hydrolysis to the amide stage as opposed to complete hydrolysis to the carboxylic acid stage. The corresponding lower alkyl-substituted amides are preferably obtained by first transforming the carboxylic function of the formula (I-a), acids into the corresponding acid chloride form, for example, by treatment of the acid or its alkali metal salt with thionyl chloride or oxalyl chloride, and then reacting the thus-obtained acid chloride with an appropriate lower alkyl-amine or di-(lower alkyl)-amine to yield the corresponding N-alkyl or N,N-dialkyl amides, respectively, of formula (I-a). Alternatively, the amides of formula (I-a) may be obtained by conventional ammonolysis of the corresponding lower alkyl esters employing ammonia, or, to prepare the substituted amides of formula (I-b), by employing an appropriately substituted amine, such as, for example, a primary lower alkylamine, a secondary lower alkylamine, an amine of the formula $H_2N$—$(CH_2)_n$—$N$-(lower alkyl)$_2$ in which $n$ is the integer 2, 3 or 4, or hydroxylamine (preferably as the hydrochloride), preferably in an alcoholic solvent at elevated temperatures and in the presence of a basic catalyst normally employed in such ester to amide transformations, e.g., sodium methoxide.

The compounds of formula (I-b), wherein $R_3$ is COO-(lower alkyl), preferably ethoxycarbonyl, and Ar is other than aminophenyl are prepared by a Friedel-Crafts reaction between an appropriate aroyl halide, preferably the chloride (VIII), and a lower alkyl 1-(lower alkyl)-pyrrole-2-propionate (IX). Conventional hydrolysis of the thus-obtained lower alkyl 5-aroyl-1-(lower alkyl)-pyrrole-2-propionate (X) yields the corresponding free acids of formula (I-b). In turn, the esters and acids may be converted to the corresponding amides of formula (I-b) according to conventional procedures as previously described for formula (I-a) using ammonia, or an appropriate alkyl or dialkyl amine.

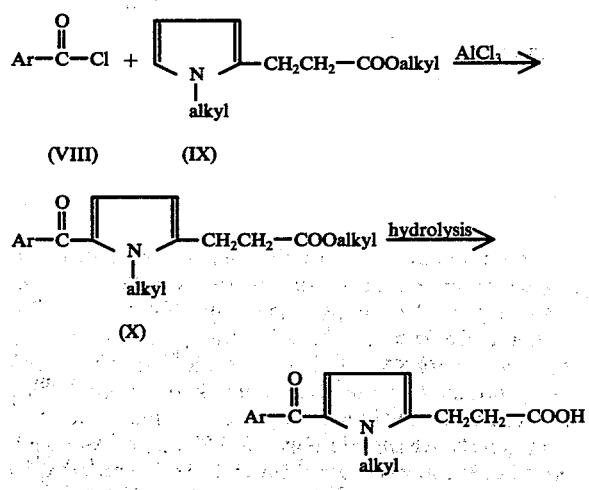

The formula (I-b) compounds, wherein Ar is aminophenyl, are preferably obtained from the corresponding lower alkyl 5-nitrobenzoyl-1-(lower alkyl)-pyrrole-2-pyrrole-2-propionate (obtained by the usual Friedel-Crafts type of reaction between nitrobenzoyl chloride and alkyl propionate (IX) by transforming the nitro function to an amino function according to the reaction scheme previously described for the formula (I-a) compounds, i.e., by means of catalyst hydrogenation followed by hydrolysis.

The alkyl propionates (IX) may be prepared by first treating an appropriate N-alkylpyrrole-2-carboxyaldehyde with an appropriate alkoxycarbonyl-methylene triphenylphosphorane [see R. Jones et al., Canad. Jour. Chem., 18, 883 (1965)] and then hydrogenating the thus-obtained alkyl 2-(1-alkyl-2-pyrrolyl)-acrylate, thereby saturating the double bond of the acrylate function, to yield the desired alkyl propionate (IX).

The compounds of formula (I-c), wherein $R_4$ is hydrogen, are prepared from an appropriate 1-aryl-1,2,3-butanetrione-2-oxime (XI) and an appropriate dialkyl acetonedicarboxylate (XII) as starting materials. The two are contacted together according to a Knorr pyrrole synthesis in glacial acetic acid in the presence of zinc dust to yield the ring-closed pyrrole, alkyl 5-aroyl-3-alkoxycarbonyl-4-methylpyrrole-2-acetate (XIII). Hydrolysis of the latter with moderately concentrated alkali, for example 25–50% aqueous sodium hydroxide gives the corresponding free di-acid (XIV), including in said hydrolysis step the liberation of said di-acid by treating the salt formed during the alkaline hydrolysis with mineral acid, which is then partially reesterified using an acidic solution of a lower alkanol to yield the corresponding alkyl 5-aroyl-3-carboxy-4-methylpyrrole-2-acetate (XV). Decarboxylation of the carboxy group in the 3-position is then accomplished by heating the latter in a suitable basic organic solvent such as quinoline to a $CO_2$-elimination temperature. The resulting alkyl 5-aroyl-4-methylpyrrole-2-acetate (XVI) is then hydrolyzed in the usual manner to give the desired free acids (XVII) of formula (I-c). In turn, the acids may be esterified using lower alkanols to the corresponding lower alkyl esters of formula (I-c) and such acids or esters are converted to the corresponding amides of formula (I-c) according to conventional procedures using ammonia, or an appropriate alkyl or dialkyl amine. The foregoing reaction sequence may be illustrated by the following diagrammatic scheme:

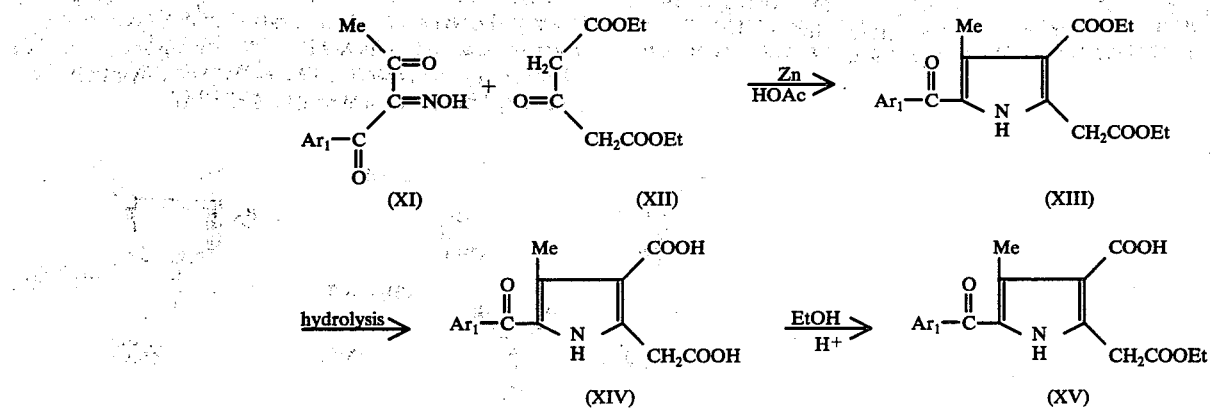

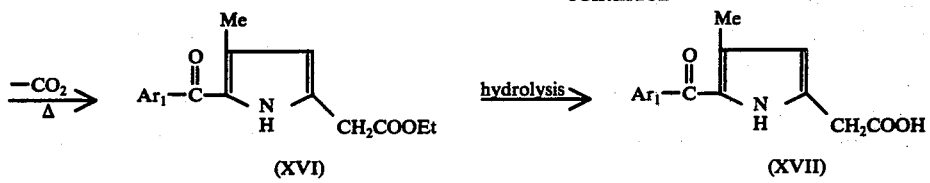

The compounds of formula (I-d) are prepared from the known pyrrole ester, ethyl 2,4-dimethylpyrrole-3-acetate (XVIII), which is acylated according to a Friedel-Crafts reaction using an appropriate benzoyl halide, preferably the chloride (XIX), as the acylating agent. The methyl group in the 2-position of the thus-obtained ethyl 5-benzoyl-2,4-dimethylpyrrole-3-acetate (XX) is then perchlorinated by treating said ester (XX) with sulfuryl chloride in an inert solvent such as ether to yield the corresponding ethyl 5-benzoyl-4-methyl-2-trichloromethylpyrrole-2-acetate (XXI). Hydrolysis of the latter, for example, by heating at reflux in aqueous dioxane or 1,2-dimethoxyethane, for a few hours, gives the di-acid, 5-benzoyl-4-methyl-2-carboxypyrrole-3-acetic acid (XXII). The carboxy function on the 2-position is then removed, for example, by heating in a suitable basic organic solvent such as quniolinе, to yield the desired free acids (XXIII) of formula (I-d). Again, the acids may in turn be converted to the corresponding esters, from which acids and esters the amides of formula (I-d) are produced in the usual manner. The foregoing reaction sequence may be illustrated by the following diagrammatic scheme:

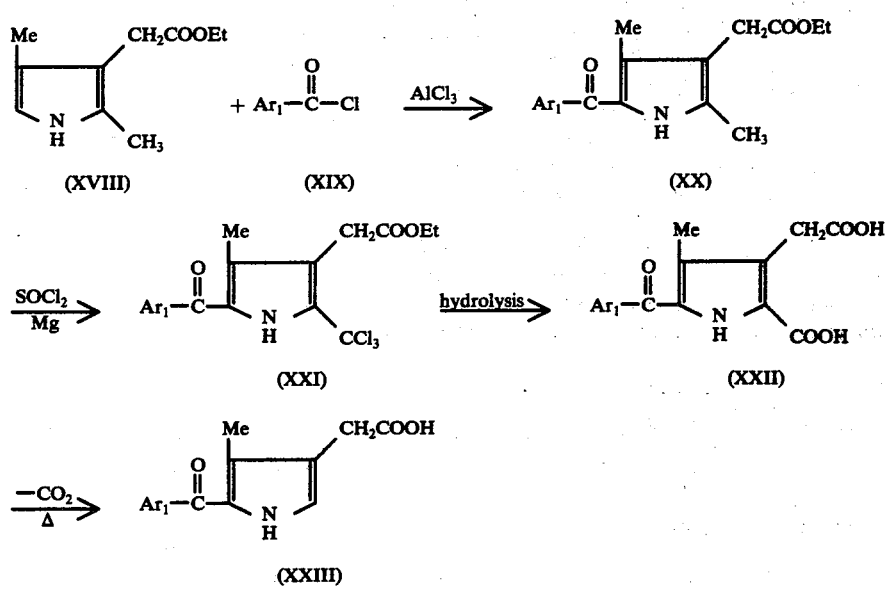

The compounds of formula (I-e), wherein $R_6$ is hydrogen, are prepared according to the following synthetic sequence. An appropriate chloromethyl loweralkyl ketone of formula XXIV is added to a minute of an appropriate di-loweralkyl acetone dicarboxylate, preferably the diethyl ester (XII), and a lower-alkylamine ($R_4$-$NH_2$), preferably in an aqueous medium. The reaction temperature is preferably maintained just below 60° C. and, after a few hours, the mixture is treated with ice-hydrochloric acid. The thus-obtained ring-closed pyrrole, alkyl 1-loweralkyl-4-loweralkyl-3-alkoxycarbonyl-pyrrole-2-acetic (XXV) is then acylated with an appropriate aroyl halide, preferably the chloride, of the formula: Ar—COCl wherein Ar is as previously described, except for phenyl substituted with lower alkoxy, amino, cyano and methylthio, under Friedel-Crafts reaction conditions to yield the corresponding alkyl 5-aroyl-1-loweralkyl-4-loweralkyl-3-alkoxycarbonyl-pyrrole-2-acetate (XXVI). The foregoing reaction scheme may be illustrated as follows (the symbols "$R_4$" and "$R_5$" being as previously described:

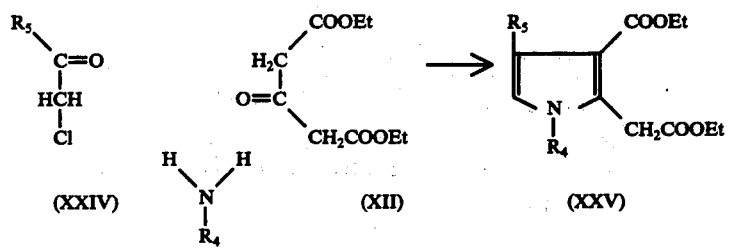

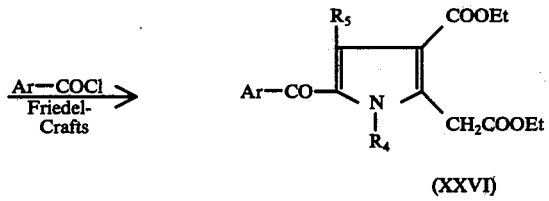

The thus-described 5-acyl product (XXVI) is then subjected to the same synthetic sequence as previously described for product (XIII) namely, the successive steps of hydrolysis, partial re-esterification, decarboxylation and hydrolysis to give the 1-$R_4$-4-$R_5$-5-acyl derivatives corresponding to products (XIV) through (XVII), respectively:

is then partially re-esterified using an acidic solution of a lower alkanol to yield the corresponding lower alkyl 1-$R_4$-4-$R_5$-3-carboxy-pyrrole-2-acetate (XXXII), the 3-position of which is then decarboxylated, for example, by heating in an inert atmosphere until gas evolution ceases or by heating in a suitable basic organic solvent such as quinoline, and the thus-obtained lower alkyl

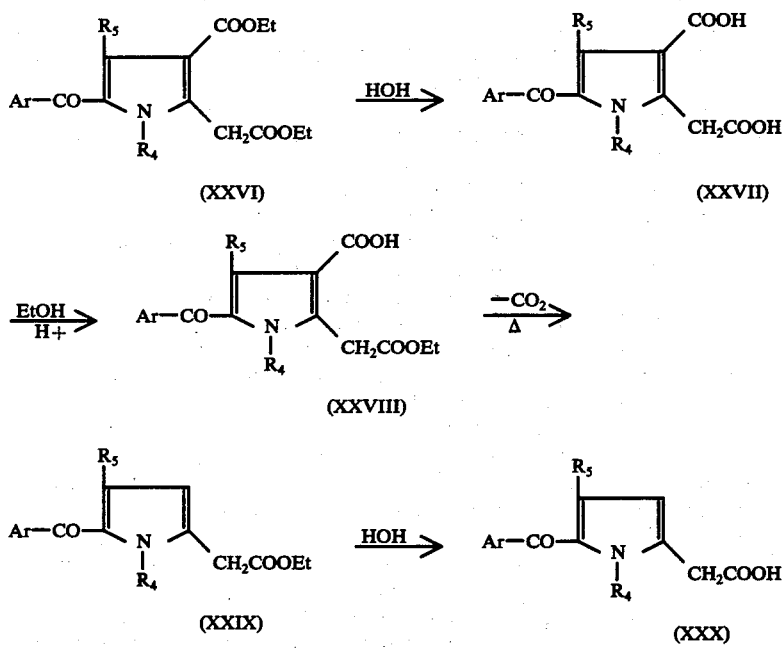

An alternative procedure for making the compounds of formula (I-e), wherein $R_6$ is hydrogen and $R_4$, $R_5$ and Ar are as previously described except that Ar is other than phenyl substituted with amino, comprises the hydrolysis of the di-ester (XXV), preferably under alkaline conditions, to the corresponding di-acid (XXXI) which 1-$R_4$-4-$R_5$-pyrrole-2-acetate (XXXIII) is then acylated with an appropriate aroyl halide, preferably the chloride, of the formula Ar-COCl under Friedel-Crafts reaction conditions to yield the corresponding ester of formula (XXXIV) which in turn may be hydrolyzed to the corresponding acid form (XXXV):

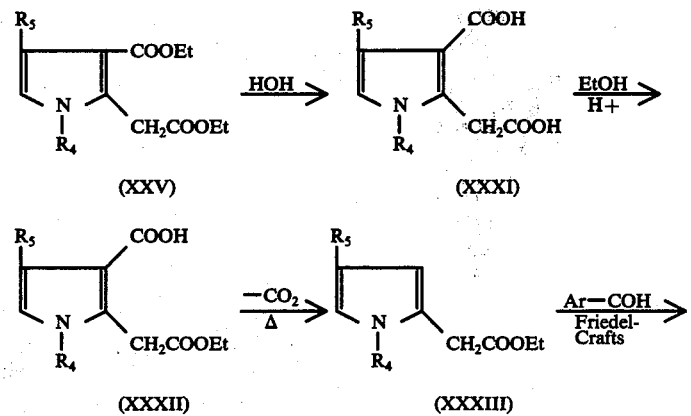

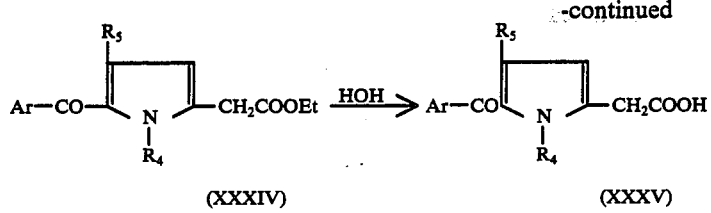

(XXXIV)                  (XXXV)

The process of making loweralkyl 1,4-di-loweralkyl-3-loweralkoxycarbonyl-pyrrole-2-acetate (XXV) and the alternative processes for making loweralkyl 1-$R_4$-4-$R_5$-5-aroylpyrrole-2-acetates as exemplified by structures (XXIX) and (XXXIV) are deemed to be novel and, as such, these processes constitute additional features of this invention.

Alkylation of the esters (XXIX) and (XXXIV) according to standard procedures, e.g., with loweralkyl iodide as the alkylating agent in the presence of a strong base such as sodium amide or sodium hydride in a suitable organic solvent such as dimethyl sulfoxide, yields the corresponding α-lower-alkyl derivatives of formula (I-e) from which the corresponding α-loweralkyl acids are obtained by conventional hydrolysis. Such acids, together with those of formulas (XXX) and (XXXV) are readily esterified and the amides and substituted amides as defined by "$R_3$" in formula (I-e) are prepared by the methods previously described herein.

The compounds of formula (I-e), wherein Ar is amino-substituted phenyl, are preferably obtained by reduction of the corresponding 5-nitrobenzoyl esters of formulas (XXIX) and (XXXIV), including the α-loweralkyl derivatives thereof, according to the method previously shown for converting the 5-nitrobenzoyl derivatives of formula (I-a) to the corresponding 5-aminobenzoyl form. Similarly, the thus-obtained lower alkyl 5-aminobenzoyl-1-$R_4$-4-$R_5$-α-$R_6$-pyrrole-2-acetates can be hydrolyzed to the corresponding free acid form from which the desired esters and amides defined by "$R_3$" of formula (I-e) may be obtained according to the usual methods previously described.

The corresponding salts of the acids of formulas (I-a, b, c, d and e) are readily obtained by treating the acids with a slight excess of an equivalent amount of appropriate base, for example, an alkali or alkaline earth metal hydroxide, e.g., sodium hydroxide, potassium hydroxide, barium hydroxide, calcium hydroxide and the like, or with an organic amine base, e.g., a lower alkylamine such as ethylamine, propylamine and the like, or other amines such as benzylamine, piperidine, pyrrolidine and the like.

The subject compounds of formulas (I-1, b, c, d and e) and the therapeutically active salts thereof have useful pharmacological properties which make them suitable for incorporation into conventional pharamceutical forms for administration. These compounds have been found to possess anti-inflammatory activity as demonstrated in the standard kaolin-induced rat paw edema and cotton pellet granuloma tests at doses generally ranging from 5-100 mg/kg body weight.

In the kaolin-induced rat paw edema assay, the ability of a compound, when administered in a single oral dose, to inhibit the swelling of the rat paw injected with a standard amount (0.1 ml.) of 10% kaolin suspension in saline is measured. For comparative purposes, the activity of the compound to be tested is measured against that produced by the known anti-inflammatory agent, phenylbutazone. Male Holtzman rats are used in the assay. For example, in this test, the compound 5-(p-chlorobenzoyl)-1-methyl-pyrrole-2-acetic acid was found to exhibit an inhibition of about 35% as 12.5 mg/kg; about 47% at 25 mg/kg; and about 45–53% inhibition in doses of 50-100 mg/kg; whereas phenylbutazone exhibited an inhibition of 30–40% at 80 mg/kg and 50–60% at 100 mg/kg.

In the cotton pallet granuloma assay, the ability of a compound, when administered orally to male Holtzman rats daily for seven days, to inhibit the amount of granuloma tissue formed in or around a cotton pellet implanted beneath the skin in the thoracic region of the animal is measured and compared to water controls. The method is described by Charles A. Winter and co-workers in J. Pharmacol., 141, 369 (1963). Analysis of variance is used to determine the significance of the results. For example, in this test, the compound 5-(p-anisoyl)-1l-methylpyrrole-2-acetic acid exhibited a granuloma weight of about 71 mg. at a dose of 25 mg/kg as compared to 110 mg. with the water controls; and the compound 5-(p-chlorobenzoyl)-1-methylpyrrole-2-acetonitrile exhibited a granuloma weight of about 98 mg. at a dose of 100 mg/kg as compared to 115 mg. with the water controls.

In the following table, the anti-inflammatory activity of several compounds of formulas (I-a, b, c, d and e) is listed, is being understood that such compounds are not listed for purposes of limiting the invention thereto, but only to exemplify the useful properties of all the compounds within the scope of formulas (I-a, b, c, d and e), including the pharmaceutically acceptable basic salts thereof.

TABLE I

| KAOLIN-INDUCED PAN EDEMA ASSAY | | |
|---|---|---|
|  | DOSE (p.o.) mg/kg | % INHIBITION (Average 10 rats) |
| 5-(p-chlorobenzoyl)-1-methylpyrrole-2-acetic acid | 25 | 47 |
| 5-(m-chlorobenzoyl)-1-methylpyrrole-2-acetic acid | 25 | 41 |
| 5-(o-chlorobenzoyl)-1-methylpyrrole-2-acetic acid | 25 | 44 |
| 5-(2',4'-dichlorobenzoyl)-1-methylpyrrole-2-acetic acid | 25 | 51 |
| 5-(p-bromobenzoyl)-1-methyl-pyrrole-2-acetic acid | 25 | 42 |
| 5-(p-flurobenzoyl)-1-methylpyrrole-2-acetic acid | 25 | 42 |
| 5-(p-methoxybenzoyl)-1-methylpyrrole-2-acetic acid | 25 | 42 |
| 5-(p-methylbenzoyl)-1-methylpyrrole-2-acetic acid | 25 | 44 |
| 5-(p-nitrobenzoyl)-1-methylpyrrole-2-acetic acid | 100 | 35 |

TABLE I-continued
KAOLIN-INDUCED PAN EDEMA ASSAY

| | DOSE (p.o.) mg/kg | % INHIBITION (Average 10 rats) |
|---|---|---|
| 5-(p-aminobenzoyl)-1-methylpyrrole-2-acetic acid | 25 | 23 |
| 5-(p-cyanobenzoyl)-1-methylpyrrole-2-acetic acid | 100 | 20 |
| 5-benzoyl-1-methylpyrrole-2-acetic acid | 25 | 38 |
| 5-(p-chlorobenzoyl)-α-methyl-1-methylpyrrole-2-acetic acid | 50 | 56 |
| 5-(p-chlorobenzoyl)-α-ethyl-1-methylpyrrole-2-acetic acid | 25 | 22 |
| 5-(p-chlorobenzoyl)-pyrrole-2-acetic acid | 25 | 32 |
| 5-(p-chlorobenzoyl)-1-ethylpyrrole-2-acetic acid | 100 | 43 |
| 1-benzyl-5-(p-chlorobenzoyl)-pyrrole-2-acetic acid | 50 | 23 |
| ethyl 5-(p-chlorobenzoyl)-1-methylpyrrole-2-acetate | 25 | 37 |
| methyl 5-(p-chlorobenzoyl)-1-methylpyrrole acetate | 25 | 38 |
| 5-(p-chlorobenzoyl)-1-methylpyrrole-2-acetamide | 50 | 35 |
| 5-(p-chlorobenzoyl)-N-ethyl-1-methylpyrrole-2-acetamide | 25 | 25 |
| 5-(p-chlorobenzoyl)-N,N-diethyl-1-methylpyrrole-2-acetamide | 25 | 36 |
| 5-(p-chlorobenzoyl)-1-methylpyrrole-2-propionic acid | 25 | 63 |
| 5-(p-chlorobenzoyl)-4-methylpyrrole-3-acetic acid | 50 | 43 |
| 5-benzolyl-4-methylpyrrole-2-acetic acid | 100 | 34 |
| (v)-5-(p-chlorobenzoyl-α-methyl-1-methylpyrrole acid | 25 | 62 |
| (-)-5-(p-chlorobenzoyl)-α-methyl-1-methylpyrrole-2-acetic acid | 25 | 24 |
| 5-(5-methylthenoyl)-1-methylpyrrole-2-acetic acid | 25 | 48 |
| 5-(2-thenoyl)-1-methylpyrrole-2-acetic acid | 25 | 63 |
| 5-(p-trifluoromethylbenzoyl-1-methylpyrrole-2-acetic acid | 25 | 60 |
| 5-(p-methylbenzoyl)-1-methylpyrrole-2-acetic acid | 12.5 | 34 |
| 5-(p-methylbenzoyl)-1-methylpyrrole-2-acetic acid pyrrole-2-acetohydroxamic acid | 25 | 33 |
| 5-(p-chlorobenzoyl)-N-(2-diethylaminoethyl)-1-methylprrole-2-acetamide | 25 | 27 |

Due to their surprisingly marked potency and/or low toxicity profile, the compounds of formula (I-e) are among the preferred compounds described herein, particularly when $R_2$ is loweralkyl (preferably methyl). For example, in the kaolin-induced rat paw edema assay, a 51% inhibition was observed with 5-(p-chlorobenzoyl)-1,4-dimethylpyrrole-2-acetic acid at a dose of 2.5 mg/kg; 29% inhibition at 3.0 mg/kg and 47% inhibition at 9.0 mg/kg with 5-(p-chlorobenzoyl)-4-ethyl-1-methylpyrrole-2-acetic acid; and 37% inhibition at 3.0 mg/kg and 53% inhibition at 9.0 mg/kg with 5-(p-chlorobenzoyl)-α-methyl-1,4-dimethyl-2l-acetic acid. Other preferred compounds are those embraced within formulas (I-a, b, c, d and e) wherein the Ar or $Ar_1$ function is halo penyl, most preferaby chlorophenyl, and the $R_2$ or $R_3$ function is COOH or COO(lower alkyl).

As anti-inflammatory agents, the compounds of formulas (I-a, b, c, d and e) and salts thereof are of value in reducing inflammation and alleviating the symptoms of rheumatic, arthritic and other inflammatory conditions. The compounds can be administered in therapeutic dosages in conventional pharmaceutical formulations for oral and parenteral administration, for example, tablets, capsules, solutions, suspensions, elixirs, injectables and the like.

As is evident from the previously described methods of forming the subject compounds, many of the compounds of formulas (I-a, b, c, d and e) are also useful as intermediates in the syntheses of other compounds thereunder. For example, the nitriles and esters represented by formulas (IV, V, VI and VII) are useful intermediates in the syntheses of corresponding acids. In addition, the 5-nitrobenzoyl compounds of formulas (I-a) and (I-b) are useful intermediates in the transformation procedure to corresponding 5-aminobenzoyl compounds. Moreover, the acids embraced within formulas (I-a, b, c, d and e) are useful intermediates in the transformation procedures to corresponding esters, amides and basic salts.

Due to the available asymmetric α-carbons present in the subject compounds of formulas (I-a) and (I-e), it is evident that their existence in the form of stereochemical isomers (enantiomorphs) is possible. If desired, the resolution and isolation or the production of a particular form can be accomplished by application of general principles known in the art. Said enantiomorphs are naturally intended to be included within the scope of this invention.

The following examples are intended to illustrate, but not to limit, the scope of the present invention.

EXAMPLE I

Ethyl 1,4-dimethyl-3-ethoxycarbonylpyrrole-2-acetate

To a solution of 500 ml. of 25% aqueous methylamine is added 93 g. (0.46 mole) of diethyl acetone-dicarboxylate. To the mixture is added 72 g. (0.782 mole) of chloroacetone over a 10 min. period. The temperature is kept below 60° C. by external cooling. After 2 hours, the mixture is poured into ice-hydrochloric acid. The solid is collected by filtration, washed with water and air dried. It is recrystallized from hexane to give ethyl 1,4-dimethyl-3-ethoxycarbonylpyrrole-2-acetate as a white solid, m.p. 71°–72° C.

Anal. Calcd. for $C_{13}H_{19}NO_4$: C, 61.64; H, 7.56; N, 5.53%. Found: C, 61.64; H, 7.64; N, 5.71%.

EXAMPLE II

Ethyl 5-(p-chlorobenzoyl)-1,4-dimethyl-3-ethoxycarbonyl-pyrrole-2-acetate

A solution of 17.5 g. (0.1 mole) p-chlorobenzoyl chloride and 13.3 g. (0.1 mole) aluminum chloride in 150 ml. of dichloroethane is added rapidly to a solution of 25.3 g. (0.1 mole) of ethyl 1,4-dimethyl-3-ethoxycarbonylpyrrole-2-acetate in 100 ml. of refluxing 1,2-dichloroethane. The solution is refluxed for 3.5 hours and poured into ice-hydrochloric acid. The organic layer is separated and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residue product is crystallized from cyclohexane and recrystallized from methanol to give ethyl 5-(p-chlorobenzoyl)-1,4 dimethyl-3-ethoxycarbonylpyrrole-2-acetate as a white solid, m.p. 91°–93° C.

EXAMPLE III

5-(p-chlorobenzoyl)-3-carboxy-1,4-dimethylpyrrole-2-acetic acid

A suspension of 17.3 g. (0.0435 mole) of ethyl 5-(p-chlorobenzoyl)-1,4 dimethyl-3-ethoxypyrrole-2-acetate in 170 g. of 25% sodium hydroxide is heated under reflux for 3 hrs. The suspension is poured into ice and the resulting yellow solution is added to ice-hydrochloric acid with stirring. The precipitated solid is collected by filtration, air dried and recrystallized from acetone containing 10% water to give 5-(p-chlorobenzoyl)-3-carboxy-1,4-dimethylpyrrole-2-acetic acid as a white solid, m.p. 253°–254° C.

EXAMPLE IV

Ethyl 5-(p-chlorobenzoyl)-3-carboxy-1,4-dimethylpyrrole-2-acetate

A suspension of 2.0 g. of 5-(p-chlorobenzoyl)-3-carboxy-1,4-dimethylpyrrole-2-acetic acid in 20 ml. of 0.5% ethanolic hydrogen chloride is heated under reflux. The solid gradually dissolves. After 40 min. a white crystalline solid precipitates. The solution is cooled and the solid product, ethyl 5-(p-chlorobenzoyl)-3-carboxy-1,4-dimethylpyrrole-2-acetate, is filtered and dried, m.p. 197°–198° C.

EXAMPLE V

Ethyl 5-(p-chlorobenzoyl)-1,4-dimethylpyrrole-2-acetate

A 9.0 g. (0.0255 mole) sample of ethyl 5-(p-chlorobenzoyl-3-carboxy-1,4-dimethylpyrrole-2-acetate is heated under nitrogen at 210° to 230° C. for 2 hrs. Gas is evolved. The residue is molecularly distilled in a sublimator at 195° C., 0.05 mm/Hg. The sublimate is recrystallized from cyclohexane to give ethyl 5-(p-chlorobenzoyl)-1,4-dimethylpyrrole-2-acetate as a white solid, m.p. 107°–109° C.

EXAMPLE VI

5-(p-chlorobenzoyl)-1,4-dimethylpyrrole-2-acetic acid

A suspension of 4.0 g. (0.0125 mole) of ethyl 5-(p-chlorobenzoyl)-1,4-dimethylpyrrole-2-acetate in 26 ml. of 0.5 N sodium hydroxide (0.013 mole) is heated under reflux for 30 mins. The resulting solution is acidified with dilute hydrochloric acid, and the precipitated solid is collected by filtration, air dried and recrystallized from 2-propanol to give 5-(p-chlorobenzoyl)-1,4-dimethylpyrrole-2-acetic acid as a white crystalline solid, m.p. 178°–179° C.

Anal. Calcd. for $C_{15}H_{14}ClNO_3$: C, 61.76; H, 4.83; N, 4.82%. Found: C, 61.68; H, 4.96; N, 4.89%.

EXAMPLE VII

Ethyl 1,4-dimethyl-3-ethoxycarbonyl-5-(p-toluoyl)-pyrrole-2-acetate

A solution of 30.8 g. p-toluoyl chloride and 26.6 g. (0.2 mole) of aluminum chloride in 250 ml. of 1,2-dichloroethane is added to a refluxing solution of 50.6 g. (0.2 mole) of ethyl 3-ethoxycarbonyl-1,4-dimethylpyrrole-2-acetate in 250 ml. of 1,2-dichloroethane over 30 min. The mixture is heated under reflux for 90 min. and poured into ice-diluted hydrochloric acid. The organic solution is separated, washed with brine, and dried over magnesium sulfate. The solvent is evaporated in vacuo and the residue is recrystallized from methanol to give ethyl 1,4-dimethyl-3-ethoxycarbonyl-5-(p-toluoyl)-pyrrole-2-acetate as a white solid, m.p. 108°–111° C.

EXAMPLE VIII

3-Carboxy-1,4-dimethyl-5-(p-toluoyl)-pyrrole-2-acetic acid

A suspension of 54 g. (0.145 mole) of ethyl 1,4-dimethyl-3-ethoxycarbonyl-5-(p-toluoyl)-pyrrole-2-acetate in 500 g. of 25% sodium hydroxide is heated at just below reflux for 3 hrs. The yellow suspension is then poured into ice-hydrochloric acid and the precipitated solid is collected, air dried and recrystallized from acetone-water to give 3-carboxy-1,4-dimethyl-5-(p-toluoyl)-pyrrole-2-acetic acid as a white solid, m.p. 229°–230° C.

Anal. Calcd. for $C_{17}H_{17}NO_5$: C, 64.75; H, 5.43; N, 4.44%. Found: C, 64.86; H, 5.53; N, 4.47%.

EXAMPLE IX

Ethyl 3-carboxy-1,4-dimethyl-5-(p-toluoyl)-pyrrole-2-acetate

A solution of 37 g. (0.118 mole) of 3-carboxy-1,4-dimethyl-5-(p-toluoyl)-pyrrole-2-acetic acid in 370 ml. of ethanol containing 1.8 g. of dry hydrogen chloride is heated under reflux for 45 min. The solution is cooled and the solid which precipitated, ethyl 3-carboxy-1,4-dimethyl-5-(p-toluoyl)-pyrrole-2-acetate, is collected, m.p. 200°–202° C.

EXAMPLE X

Ethyl 1,4-dimethyl-5-(p-toluoyl)-pyrrole-2-acetate

A solution of 33.0 g. (0.096 mole) of ethyl 3-carboxy-1,4-dimethyl-5-(p-toluoyl)-pyrrole-2-acetate in 200 ml. of quinoline with 0.1 g. copper chromite added is heated under nitrogen for 6 hr. at 200° C., then for 30 min. at 220° C. The quinoline is distilled off in vacuo. The residue is dissolved in ether and washed successively with dilute hydrochloric acid, dilute sodium hydroxide, and brine; dried over magnesium sulfate; and the solvent evaporated in vacuo to give a brown oily residue which crystallizes. It is recrystallized from methanol, sublimed at 150° C. (0.025 mm/Hg) and recrystallized from hexane to give ethyl 1,4-dimethyl-5-(p-toluoyl)-pyrrole-2-acetate as a white solid, m.p. 90°–93° C.

EXAMPLE XI

1,4-Dimethyl-5-(p-toluoyl)-pyrrole-2-acetic acid

A suspension of 8.5 g. (0.0284 mole) of ethyl 1,4-dimethyl-5-(p-toluoyl)-pyrrole-2-acetate in 29 ml. of 1N sodium hydroxide solution is heated under reflux for 20 min. The yellow solution is diluted with water and added to dilute hydrochloric acid. The precipitated solid is collected, dried in vacuo, and recrystallized from 2-propanol to give 1,4-dimethyl-5-(p-toluoyl)-pyrrole-2-acetic acid as a white solid, m.p. 160°–161° C.

Anal. Calcd. for $C_{16}H_{17}NO_3$: C, 70.83; H, 6.32; N, 5.16%. Found: C, 70.90; H, 6.39; N, 5.25%.

EXAMPLE XII

By following the procedures outlined in Examples II through VI, except that an equivalent quantity of benzoyl chloride and 2,3,5-tribromobenzoyl chloride is employed as the starting acylating agent in place of the p-chlorobenzoyl chloride used in Example II, there are obtained, as the respective products of each Example, the corresponding 5-benzoyl and 5-(2,3,5-tribromobenzoyl) derivatives.

EXAMPLE XIII

Lower alkyl esters of the acids obtained in Examples VI, XI and XII are prepared by standard esterification techniques using an appropriate lower alkanol. Typical of such esters are the following products:

n-propyl 5-(p-chlorobenzoyl)-1,4-dimethylpyrrole-2-acetate;
n-butyl 5-(p-toluoyl)-1,4-dimethylpyrrole-2-acetate;
ethyl 5-benzoyl-1,4-dimethylpyrrole-2-acetate;
isobutyl 5-(2,3,5-tribromobenzoyl)-1,4-dimethylpyrrole-2-acetate.

EXAMPLE XIV

Primary, secondary and tertiary amides of the acids obtained in Examples VIII, XI and XIII are prepared by conventional procedures, for example, by treatment with thionyl chloride and then reacting the thus-obtained acid chloride with either ammonia, a primary lower alkylamine or a secondary lower alkylamide. Typical of such amides are the following products:

5-(p-chlorobenzoyl)-1,4-dimethylpyrrole-2-acetamide;
5-(p-chlorobenzoyl)-N-methyl-1,4-dimethylpyrrole-2-acetamide;
5-(p-toluoyl) 1,4-dimethylpyrrole-2-acetamide;
5-(p-toluoyl)-N,N-diethyl-1,4-diethylpyrrole-2-acetamide;
5-benzoyl-N-propyl-1,4-dimethylpyrrole-2-acetamide;
5-(2,3,5-tribromobenzoyl)-1,4-dimethylpyrrole-2-acetamide.

EXAMPLE XV

A. 1-Chloro-2-butanone

Chlorination of methylethylketone is carried out according to Bruylant and Houssiau [Bull. Soc. Chem. Belg., 6, 492 (1952)]. The mixture obtained is fractionally distilled at atmospheric pressure through a Vigreaux column. The fraction boiling at 135°–144° C. is shown by vapor phase chromatography to contain approximately 75% 1-chloro-2-butanone and 25% 3-chloro-2-butanone. This fraction may be used in the next example without further separation.

B. According to the procedure described by Bruylant and Houssiau (see above), chlorination of an appropriate methyl loweralkyl ketone followed by fractional distillation yields the corresponding chloromethyl loweralkyl ketones of formula (XXIV), such as, for example, chloromethyl n-butyl ketone derived from 2-hexanone.

EXAMPLE XVI

Ethyl 3-ethoxycarbonyl-4-ethyl-1-methylpyrrole-2-acetate

A 900 ml. solution of 25% aqueous methylamine is cooled in an ice bath and 101 g. (0.5 mole) of diethyl acetone decarboxylate is added. To the mixture is added 110 g. of the 1-chloro-2-butanone mixture obtained in Example XV. Intermittent cooling is applied to keep the temperature below 60° C. The mixture is stirred for one hour and poured into ice-hydrochloric acid. The crystalline product is collected by filtration and recrystallized from methanol to yield ethyl 3-ethoxycarbonyl-4-ethyl-1-methylpyrrole-2-acetate as a white solid, m.p. 65°–67° C.

EXAMPLE XVII

Ethyl (5-p-chlorobenzoyl)-3-ethoxycarbonyl-4-ethyl-1-methylpyrrole-2-acetate A solution of 13.8 g. (0.0788 mole) of p-chlorobenzoyl chloride and 10.5 g. (0.0788 mole) of aluminum chloride in 120 ml. of 1,2-dichloroethane is added to a refluxing solution of 21.8 g. (0.0788 mole) of ethyl 3-ethoxycarbonyl-4-ethyl-1-methylpyrrole-2-acetate. The mixture is heated under reflux for 10 hrs. and stirred at room temperature for an additional 10 hrs. It is then poured into ice-hydrochloric acid. The organic layer is separated and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residual red oily residue crystallizes on standing. It is recrystallized twice from methanol to give ethyl (5-o-chlorobenzoyl)-3-ethoxycarbonyl-4-ethyl-1-methylpyrrole-2-acetate as a white solid, m.p. 72°–74° C.

EXAMPLE XVIII

3-Carboxy-5-(p-chlorobenzoyl)-4-ethyl-1-methylpyrrole-2-acetic acid

A suspension of 18.2 g. (0.044 mole) of ethyl 5-(p-chlorobenzoyl)-3-ethoxycarbonyl-4-ethyl-1-methylpyrrole-2-acetate in 170 ml. of 25% aqueous sodium hydroxide solution is heated under reflux for 3 hrs. It is cooled, diluted with water and acidified with dilute hydrochloric acid. The precipitated solid is collected by filtration and air dried. It is recrystallized from acetone-water to give 3-carboxy-5-(p-chlorobenzoyl)-4-ethyl-1-methylpyrrole-2-acetic acid, m.p. 211°–212.5° C.

EXAMPLE XIX

Ethyl 3-carboxy-5-(p-chlorobenzoyl)-4-ethyl-1-methylpyrrole-2-acetate

A solution of 13.8 g. (0.0375 mole) of 3-carboxy-5-(p-chlorobenzoyl)-4-ethyl-1-methylpyrrole-2-acetic acid in 140 ml. of 0.5% ethanolic hydrogen chloride is heated under reflux for 45 min. After cooling, the precipitated solid is collected. A second crop is obtained by partial evaporation of the solvent, recrystallized from ethanol and combined with the first crop to give ethyl 3-carboxy-5-(p-chlorobenzoyl)-4-ethyl-1-methylpyrrole-2-acetate, m.p. 185°–186° C.

EXAMPLE XX

Ethyl 5-(p-chlorobenzoyl)-4-ethyl-1-methylpyrrole-2-acetate

A 13.7 g. (0.035 mole) sample of ethyl 3-carboxy-5-(p-chlorobenzoyl)-4-ethyl-1-methylpyrrole-2-acetate is heated at 200° to 210° C. under nitrogen for 90 min. The resulting oil is molecularly distilled at 185° C. and 0.1 mm pressure to yield a solid which is recrystallized from cyclohexane and then methanol to give ethyl 5-(p-chlorobenzoyl)-4-ethyl-1-methylpyrrole-2-acetate as a white solid, m.p. 73°–75° C.

EXAMPLE XXI

5-(p-Chlorobenzoyl)-4-ethyl-1-methylpyrrole-2-acetic acid

A suspension of 4.5 g. (0.0136 mole) of ethyl 5-(p-chlorobenzoyl)-4-ethyl-1-methylpyrrole-2-acetate in 28 ml. 0.5 N sodium hydroxide and 1 ml. of ethanol is heated under reflux for 30 min. The mixture is then poured into ice-dilute hydrochloric acid. The precipitated solid is filtered, air dried and recrystallized from 2-propanol to give 5-(p-chlorobenzoyl)-4-ethyl-1-methylpyrrole-2-acetic acid as a white solid, m.p. 129°–131° C.

Anal. Calcd. for $C_{16}H_{16}ClNO_3$: C, 62.85; H, 5.29; N, 4.58%. Found: C, 62.58; H, 5.40; N, 4.83%.

EXAMPLE XXII

By following the procedures outlined in Examples XVII through XXI, except that an equivalent quantity of benzoyl chloride and 2,3,5-tribromobenzoyl chloride is employed as the starting acylating agent in place of the p-chlorobenzoyl chloride used in Example XVII there are obtained, as the respective products of each Example, the corresponding 5-benzoyl and 5-(2,3,5-tribromobenzoyl) derivatives.

EXAMPLE XXIII

Ethyl 5-(p-chlorobenzoyl)-1,4,α-trimethylpyrrole-2-acetate 6.4 Grams (0.02 mole) of ethyl 5-(p-chlorobenzoyl)-1,4-dimethylpyrrole-2-acetate is dissolved in 100 ml. of dimethyl sulfoxide (DMSO) and added to a slurry of 0.48 g. (0.02 mole) of sodium hydride in approximately 30 ml. of DMSO. The mixture is stirred for 30 mins. before 2.84 g. (0.02 mole) of methyl iodide is added. Stirring is continued for 15 mins. The reaction mixture is then poured into water and the precipitate filtered off and recrystallized from 2-propanol to yield ethyl 5-(p-chlorobenzoyl)-1,4,α-trimethylpyrrole-2-acetate, m.p. 88°–90° C.

EXAMPLE XXIV

5-(p-Chlorobenzoyl)-1,4,α-trimethylpyrrole-2-acetic acid

An ethanol solution of 2.9 g. (0.0087 mole) of ethyl 5-(p-chlorobenzoyl)-1,4,α-trimethylpyrrole-2-acetate is added to 17.5 ml. 0.5 N sodium hydroxide solution and the mixture is heated under reflux for 1 hour. The ethanol is evaporated in vacuo and the solution poured into dilute hydrochloric acid. The precipitated solid is collected by filtration and recrystallized from ether-cyclohexane to give 5-(p-chlorobenzoyl)-1,4,α-trimethylpyrrole-2-acetic acid as a white solid, m.p. 153°–154° C.

Anal. Calcd. for $C_{16}H_{16}ClNO_3$: C, 62.85; H, 5.29; N, 4.58%. Found: C, 62.74; H, 5.22; N, 4.47%.

EXAMPLE XXV

A. The methylation procedure of Example XXIII is repeated, except that an equivalent quantity of each ester obtained from Examples X, XIII and XX is methylated instead of the ethyl 5-(p-chlorobenzoyl)-1,4-dimethylpyrrole-2-acetate used in Example XXIII, to yield, as respective products, the corresponding α-methyl derivative of each such ester.

B. The hydrolysis procedure of Example XXIV is followed in transforming the α-methyl esters obtained in Example XXV-A into the corresponding α-methyl acids.

C. Primary, secondary and tertiary amides of the acids obtained in Examples XXI, XXIV and XXV-B are obtained by conventional treatment with thionyl chloride and then reacting the thus-obtained acid chloride with either ammonia, a primary lower alkylamine or a secondary lower alkylamine.

D. Primary, secondary and tertiary amides of the acids obtained in A and B of this Example are prepared by conventional procedures to yield, for example, the following respective amides:

5-(p-chlorobenzoyl)-4-methylpyrrole-3-acetamide;
5-benzoyl-N-ethyl-4-methylpyrrole-3-acetamide;
5-(p-methoxybenzoyl)-N-n-propyl-4-methylpyrrole-3-acetamide;
5-(2',4'-dichlorobenzoyl)-N,N-diethyl-4-methylpyrrole-3-acetamide.

EXAMPLE XXVI

A. 2-Dimethylaminomethyl-1-benzylpyrrole

A solution of 8.2 g. (0.1 mole) dimethylamine hydrochloride in 8 ml. formalin is added dropwise to 17.12 g. (0.1 mole) of 1-benzylpyrrole. The mixture is stirred at room temperature until solution occurs (about 4 hours). The solution is poured into 10% sodium hydroxide solution and then extracted into ether three times. The combined organic fractions are washed with a saturated solution of sodium chloride, dried over magnesium sulfate and the solvent evaporated in vacuo. The product, 2-dimethylaminomethyl-1-benzylpyrrole, is distilled at reduced pressure, b.p. 73° C., 0.025 mm. Hg.

B. 2-Dimethylaminomethyl-1-benzylpyrrole methiodide

A solution of 100 g. (0.47 mole) of 2-dimethylaminomethyl-1-benzylpyrrole in 200 ml. of absolute ethanol is cooled to 5° C. To this is added dropwise 29.4 ml. (0.47 mole) of methyl iodide. A white solid precipitates. The suspension is stirred until the precipitate is so thick that additional stirring becomes impossible. The solid, 2-dimethylaminomethyl-1-benzylpyrrole methiodide, is filtered off and dried in vacuum.

What is claimed is:

1. The process of making a loweralkyl 5-aroyl-1-$R_4$-4-$R_5$-pyrrole-2-acetate of the formula:

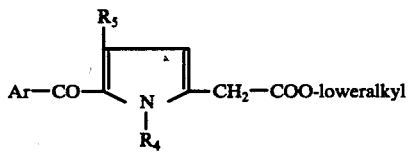

which comprises acylating a loweralkyl 1-$R_4$-4-$R_5$-3-loweralkoxy-carbonyl-pyrrole-2-acetate with an aroyl chloride of the formula Ar-COCl in the presence of a Lewis acid in an organic solvent suitable for Friedel-Crafts acylation reactions, hydrolyzing the thus-obtained loweralkyl 5-aroyl-1-$R_4$-4-$R_5$-3-loweralkoxycarbonyl pyrrole-2-acetate under alkaline conditions to form the corresponding alkaline salt of the di-acid, 5-aroyl-1-$R_4$-4-$R_5$-3-carboxypyrrole-2-acetic acid, separating said alkaline salt and treating same with strong mineral acid to form said di-acid, partially reesterifying said di-acid by treatment with an acidic solution of a lower alkanol and decarboxylating the 3-carboxy group of the thus-obtained loweralkyl 5-aroyl-1-$R_4$-4-$R_5$-3-carboxypyrrole-2-acetate by heating said loweralkyl 5-aroyl-1-$R_4$-4-$R_5$-3-carboxypyrrole-2-acetate to $CO_2$-elimination temperatures; wherein the foregoing said Ar-CO is a member selected from the group consisting of benzoyl, thenoyl, 5-methyl-thenoyl, monosubstituted benzoyl, disubstituted benzoyl and trisubstituted benzoyl, each substituent of said substituted benzoyl being a member selected from the group consisting of halo, loweralkyl, trifluoromethyl and nitro, and said $R_4$ and said $R_5$ each represent loweralkyl.

2. The process of claim 1, wherein said loweralkyl 1-$R_4$-4-$R_5$-3-loweralkoxycarbonyl-pyrrole-2-acetate is ethyl 1,4-dimethyl-3-ethoxycarbonyl-pyrrole-2-acetate.

UNITED STATES PATENT AND TRADEMARK OFFICE
CERTIFICATE OF CORRECTION

PATENT NO. : 4,070,368

DATED : January 24, 1978

INVENTOR(S) : John Robert Carson

It is certified that error appears in the above-identified patent and that said Letters Patent are hereby corrected as shown below:

At Column 1, Line 8, after "U.S. Pat. No." delete "b".
At Column 3, Line 37, after "Ar'" delete "O".
At Column 7, Line 11, after "2,4-dimethylpyrrole-" delete "b".
At Column 8, Line 39, "minute" should be -- mixture --.
At Column 8, Line 48, "-2-acetic" should be -- -2-acetate --.
At Column 11, Line 52, "(I-1" should be -- (I-a --.
At Column 11, Line 55, "pharamceutical" should be
    -- pharmaceutical --.
At Column 12, Line 26, "as" should be -- at --.
At Column 12, Line 31, "pallet" should be -- pellet --.
At Column 12, Line 41, "anisoyl)-11-" should be -- anisoyl)-1- --
At Column 12, Table I, "Pan" should be -- Paw --.
At Column 13, Table I, after "methyl 5-(chlorobenzoyl)-1-
    methylpyrrole" add -- 2 --.
At Column 13, Table I, Line 24, "(v)" should be -- (+) --.
At Column 13, Table I, Line 25, after "1-methylpyrrole" add
    -- -2-acetic --.
At Column 13, Line 30, after "(p-trifluoromethylbenzoyl" add
    -- ) --.
At Column 13, Line 46, "-21-" should be -- 2 --.
At Column 13, Line 49, "penyl" should be -- phenyl --.
At Column 16, Line 22, "diluted" should be -- dilute --.
At Column 17, Line 47, "alkylamide" should be -- alkylamine --.
At Column 17, Line 54, "diethylpyrrole" should be
    -- dimethylpyrrole --.

UNITED STATES PATENT AND TRADEMARK OFFICE
CERTIFICATE OF CORRECTION

PATENT NO. : 4,070,368
DATED : January 24, 1978
INVENTOR(S) : John Robert Carson Page 2 of 2

It is certified that error appears in the above-identified patent and that said Letters Patent are hereby corrected as shown below:

At Column 18, Line 51, "(5-o-" should be -- (5-p- --.
At Column 20, Line 37 through Column 21, Line 4 -- delete all material.

Signed and Sealed this

Twelfth Day of December 1978

[SEAL]

Attest:

RUTH C. MASON
Attesting Officer

DONALD W. BANNER
Commissioner of Patents and Trademarks